US009486653B2

(12) United States Patent
Rittner et al.

(10) Patent No.: US 9,486,653 B2
(45) Date of Patent: Nov. 8, 2016

(54) EMERGENCY OXYGEN SUPPLY MASK AND EMERGENCY OXYGEN SUPPLY ARRANGEMENT ADAPTED FOR RESCUING A PASSENGER OF AN AIRCRAFT IN AN EMERGENCY SITUATION, METHOD OF RESCUING A PASSENGER OF AN AIRCRAFT IN AN EMERGENCY SITUATION

(71) Applicant: INTERTECHNIQUE, Plaisir (FR)

(72) Inventors: Wolfgang Rittner, Ahrensbok (DE); Rüdiger Meckes, Berkenthin (DE); Günter Boomgaarden, Scharbeutz (DE); Marco Hollm, Rosdorf (DE)

(73) Assignee: Zodiac Aerotechnics, Plaisir (FR)

( * ) Notice: Subject to any disclaimer, the term of this patent is extended or adjusted under 35 U.S.C. 154(b) by 387 days.

(21) Appl. No.: 13/929,820

(22) Filed: Jun. 28, 2013

(65) Prior Publication Data
US 2014/0007869 A1    Jan. 9, 2014

Related U.S. Application Data

(60) Provisional application No. 61/665,486, filed on Jun. 28, 2012.

(51) Int. Cl.
*A62B 7/08*    (2006.01)
*A62B 7/14*    (2006.01)
(Continued)

(52) U.S. Cl.
CPC ............. *A62B 7/08* (2013.01); *A61M 16/20* (2013.01); *A62B 7/00* (2013.01); *A62B 7/02* (2013.01);
(Continued)

(58) Field of Classification Search
CPC .......... A62B 7/08; A62B 9/02; A62B 19/00; A62D 9/00; B64D 2231/00; B64D 2231/02; B64D 2231/025

USPC ................................. 95/902; 96/121, 129
See application file for complete search history.

(56) References Cited

U.S. PATENT DOCUMENTS 4,793,342 A * 12/1988 Haber ................... A62B 17/04
128/202.27
5,115,804 A * 5/1992 Brookman ........... A62B 18/025
128/201.22
(Continued)

FOREIGN PATENT DOCUMENTS

CN          1990067        7/2007

OTHER PUBLICATIONS

Ceca, "Medical oxygen concentrator (MEDOX)", retrieved from https://web.archive.org/web/20130303085909/http://www.cecachemicals.com/en/expertise/molecular-sieves/medical-oxygen-concentrators/index.html with date Mar. 3, 2013.*
(Continued)

*Primary Examiner* — Tan-Uyen (Jackie) T Ho
*Assistant Examiner* — Joseph D Boecker
(74) *Attorney, Agent, or Firm* — Kilpatrick Townsend & Stockton LLP; Dean W. Russell; Anthony L. Guebert

(57) ABSTRACT

The invention relates to a method and an emergency oxygen supply mask adapted for rescuing a passenger of an aircraft in an emergency situation. In one example, the oxygen mask includes a mask body with a first opening for covering the mouth and/or nose of a passenger and with a second opening connecting the first opening for providing breathable supply air. In some cases, the emergency oxygen supply mask includes a physical reaction component connected to the mask body for receiving air and converting the air into supply air by a physical reaction between the air and a physical reaction material in the physical reaction component to produce oxygen-enriched air. The oxygen-enriched air may be supplied as the supply air to the first opening of the mask body.

9 Claims, 3 Drawing Sheets

(51) Int. Cl.
   *A62B 18/02*   (2006.01)
   *A61M 16/20*   (2006.01)
   *A62B 7/00*    (2006.01)
   *B64D 11/00*   (2006.01)
   *A62B 7/02*    (2006.01)
   *A62B 21/00*   (2006.01)
   *A62B 9/02*    (2006.01)
   *B64D 10/00*   (2006.01)
   *G08B 5/22*    (2006.01)
   *G08B 5/00*    (2006.01)
   *G08B 5/36*    (2006.01)

(52) U.S. Cl.
   CPC . *A62B 7/14* (2013.01); *A62B 9/02* (2013.01); *A62B 18/02* (2013.01); *A62B 21/00* (2013.01); *B64D 10/00* (2013.01); *B64D 11/0015* (2013.01); *B64D 11/00155* (2014.12); *B64D 2231/00* (2013.01); *B64D 2231/02* (2013.01); *G08B 5/00* (2013.01); *G08B 5/224* (2013.01); *G08B 5/36* (2013.01)

(56) References Cited

U.S. PATENT DOCUMENTS

| | | | | |
|---|---|---|---|---|
| 5,394,867 A * | 3/1995 | Swann | | A62B 19/02 128/201.25 |
| 5,850,833 A * | 12/1998 | Kotliar | | A61G 10/00 128/202.12 |
| 6,340,024 B1 * | 1/2002 | Brookman | | A62B 17/04 128/201.15 |
| 6,478,850 B1 * | 11/2002 | Warren | | B01D 53/047 95/130 |
| 7,066,985 B2 * | 6/2006 | Deane | | B01D 53/0415 128/205.12 |
| 7,329,304 B2 * | 2/2008 | Bliss | | B01D 53/0407 128/204.21 |
| 8,016,925 B2 * | 9/2011 | McCombs | | A61M 16/10 128/205.11 |
| 8,794,237 B2 * | 8/2014 | Wilkinson | | A61M 16/0672 128/200.24 |
| 2004/0134493 A1 * | 7/2004 | McCombs | | A61M 16/0045 128/202.26 |
| 2004/0245390 A1 * | 12/2004 | Meckes | | A62B 7/14 244/118.5 |
| 2005/0051029 A1 * | 3/2005 | Lloyd | | B01D 53/0431 96/109 |
| 2008/0202511 A1 * | 8/2008 | Meckes | | B64D 10/00 128/202.26 |
| 2014/0000594 A1 | 1/2014 | Rittner et al. | | |

OTHER PUBLICATIONS

First Office Action in Chinese Patent Application No. CN201310269699.7, mailed Jan. 28, 2016, 10 pages (6 pages for translation, 4 pages for Chinese Office Action).

* cited by examiner

EMERGENCY OXYGEN SUPPLY MASK AND EMERGENCY OXYGEN SUPPLY ARRANGEMENT ADAPTED FOR RESCUING A PASSENGER OF AN AIRCRAFT IN AN EMERGENCY SITUATION, METHOD OF RESCUING A PASSENGER OF AN AIRCRAFT IN AN EMERGENCY SITUATION

CROSS-REFERENCE TO RELATED APPLICATION

This application claims the benefit of and priority to U.S. Provisional Application No. 61/665,486 filed on Jun. 28, 2012, the contents of which are incorporated herein by reference.

FIELD OF THE INVENTION

The invention relates to an emergency oxygen supply mask adapted for rescuing a passenger of an aircraft in an emergency situation and an emergency oxygen supply arrangement, in particular comprising a passenger service unit, adapted for rescuing a passenger of an aircraft in an emergency situation. Further the invention relates to a method of rescuing a passenger of an aircraft in an emergency situation.

BACKGROUND OF THE INVENTION

Passenger service units of the aforementioned type are known in the state of the art and are widely used in civil aircrafts. Generally a passenger service unit comprises a reading light, a passenger air supply device, oxygen masks, warning lights and the like appliances. In some aircrafts one passenger service unit is provided for each seat of a passenger and crew member. In other aircrafts one single passenger service unit is provided for a number of the seats, e.g. in particular for a row of seats. A row usually is aligned crosswise to an alley of seats; a row may have two, three, four, five, six or more seats depending on the size of the civil aircraft. Modern civil aircrafts cabins may have a capacity of several hundred seats for passengers.

Emergency situations on board of an aircraft may be characterized by a decompression of the cabin, smoke or fire, wind turbulences and mechanical impacts or the like. Generally an emergency situation is to be understood any kind of situation wherein a use of an oxygen mask is advisable in an aircraft. Usually, a pilot will seek to conduct a quick emergency descent of the aircraft in such an emergency situation and to reach the closest airport or emergency landing lane. However, a descent of the aircraft may require more time than estimated. However, also after landing the aircraft, a quick exit of all passengers out of the aircraft may be required. Such quick exit may be hindered by smoke and/or insufficient oxygen in the aircraft passenger cabin.

It is known to supply oxygen to passengers in an emergency situation like a situation mentioned above, in particular a decompression situation and/or a situation accompanied by development of smoke or fire in the cabin. Especially for these kinds of situation, oxygen masks drop out of a passenger service unit and oxygen is supplied to the passenger via said oxygen mask. Usually the oxygen mask is connected to the passenger service unit via a connecting line. In the passenger service unit a common oxygen source is comprised which stores oxygen and provides said oxygen to the passenger after activation of the oxygen supply, preferably to a plurality of emergency oxygen supply masks.

Usually, the passenger can activate the oxygen supply pulling a connecting line wherein said connecting line may be a flexible tube which at the same time serves to direct the oxygen from the passenger service unit to the oxygen mask or maybe a wire or rope or the like distinct from the connecting line.

It is known to store oxygen in the passenger service unit in a chemically bound form and to produce said oxygen in a chemical reaction after activation. This type of oxygen source is called chemical oxygen generator (COG).

It is further known to store oxygen in a pressurized tank wherein activation of said oxygen source comprises opening a valve or a sealing component to open said pressure tank and allow flow of oxygen out of said tank to the oxygen mask. It is known to provide an emergency oxygen supply mask of this known kind with a re-breather-bag or concentrator or the like to improve an oxygen supply to the passenger.

In particular for a pilot or a crew member of an aircraft it is known to provide On-Board Oxygen System (OBOGS) units have been used. Such OBOGS units use a microcellular sieve to filter the nitrogen out of the air to supply oxygen enriched breathable air. They are able to literally "produce its own oxygen" by means of depleting ambient air. It is possible to produce output gases which are enriched up to 95% percent of oxygen. Such an OBOGS unit is known to supply oxygen to pilots of a military aircraft.

Nevertheless such kind emergency oxygen devices have shown to be insufficient in certain emergency situations, in particular in case of smoke or fire in the cabin or during the quick exit of the passengers out of the cabin or in situations wherein estimated amount of oxygen available from a common oxygen source runs to a limit.

SUMMARY OF THE INVENTION

Accordingly, it is a major object of the present invention to provide an emergency oxygen supply device and a method adapted for rescuing a passenger of an aircraft in an emergency situation of improved kind as compared to the prior art. At least one of the above-mentioned problems should be addressed by the invention. In particular it is an object of the invention to provide an alternative solution to a solution of the prior art. It is a particular object of the invention to provide an emergency oxygen supply device and method for passengers of an aircraft which improves the safety of the passenger in above mentioned emergency situations and facilitates improved handling of the emergency oxygen supply device by the passenger. In particular it is an object of the present invention to provide an oxygen supply device and a method for rescuing a passenger of an aircraft in an emergency situation which is available in a more flexible way as compared to known concepts wherein oxygen is provided by a common oxygen source. In particular availability and mobility of an oxygen supply device shall be improved by the invention. In particular further an oxygen supply device shall be handled by a passenger in an easy and mobile way.

The object with regard to the device is achieved by the invention with an emergency oxygen supply mask as claimed in instant claim 1.

The invention starts from an emergency oxygen supply mask adapted for rescuing a passenger of an aircraft in an emergency situation has a mask body with a first opening for covering mouth and/or nose of the passenger and a second opening connecting said first opening for providing breathable supply air. In prior art concepts the second opening is connected to a somewhat common oxygen source, in particular centralized oxygen source. The invention starts from the consideration that a flow path, like an oxygen flow conduct or the like, connected therewith binds the passenger to the oxygen mask at the location place of the oxygen flow conduct; even more, in general, the passenger is advised to stay at its place and use oxygen from the flow path as long as possible. However, the invention recognized that in situations where the passenger urgently has to move—like for instance in hazardous situations to escape from fire or dust or when leaving an airplane or even for switching place to afford oxygen supply from another mask—still a supply of oxygen is essential to successful rescue a passenger or at least avoid hypoxia.

Starting from these considerations the instant invention conceptionally claims for an emergency oxygen supply mask which allows to be movable with a passenger without being bound to the place of oxygen flow conduct to the mask body. Namely, according to the concept of the invention, the oxygen mask comprises a physical reaction component connected to the mask body for receiving exhaled air out of said mask body, adapted for converting said exhaled air into supply air by a physical reaction between said exhaled air and a physical reaction material in said physical reaction component to produce oxygen-enriched air, and for supplying said oxygen-enriched air as the supply air to the first opening of the mask body, and the physical reaction component is, in particular releasable, connected to a pressurized reservoir or manifold of air.

Thus, the concept of the invention in short terms uses exhaled air of the passenger to provide a self-sustained flow of oxygen-enriched air as supply air to the mask body wherein oxygen-enrichment is achieved by a physical reaction. Oxygen-enrichment is to be understood in broad means as any kind of conditioning purifying or other kind of physical reprocessing of exhaled air resulting in a oxygen-enriched product gas stream usable as supply air to the mask body. An oxygen-enriched product gas stream is to be understood as any kind of gas stream with increased oxygen as compared to a reference flow of air, in particular exhaled air.

The physical reaction component is releasable connected to a pressurized reservoir or manifold of air. Thus in stationary use the mask body can be connected to a pressurized reservoir of air or a bleed air of the aircraft. As example thereby pressure levels in the range of already 100 mbar to 200 mbar or there above in the range of 200 mbar to 500 mbar, in particular in a range of 100 mbar to 1 bar above atmospheric pressure can be used to operate the physical reaction component as a highly efficient OBOGS system loaded with additional pressure amplitude of pressurized air. In a mobile use the mask body can be disconnected from the pressurized reservoir of air or bleed air of the aircraft and can be operated with a lower pressure, in particular the alternating breathing pressure, which e.g. is in a somewhat lower pressure range of some mbar. Still nevertheless this allows to move with the mask in a hazardous situation and nevertheless a sufficient oxygen supply is available to avoid the danger of hypoxia. Thus in short terms the invention basically provides an OBOGS system directly to the mask, namely in particular an OBOGS physical reaction component on the mask body, more particular a micro-filter or sieve-component adapted to diffuse O2 to deplete ambient or pressurized air from O2 to generate oxygen-enriched air as the supply air to the first opening of the mask body. This principle is in work at least in a stationary use when the mask body is connected to a pressurized reservoir of air or a bleed air of the aircraft. However, in a non-stationary use, preferably when the mask body is dis-connected from a pressurized reservoir of air or bleed air of the aircraft, still the physical reaction component on the mask body is partly working with less oxygen enrichment or with very diminished or no oxygen enrichment from ambient air but still at least allows to filter the ambient air and thus has a positive effect on the supply air to the first opening of the mask body.

In essence the concept of the invention allows a passenger to move with the emergency oxygen supply mask away from his place of seat. Thus a passenger is independent of a common, in particular fixed and/or central, oxygen supply conduct to a central oxygen source. This allows a passenger in hazardous situations as described in the introduction to move away from his seat to an emergency exit and wherein the passenger still is being supplied with breathable supply air, namely oxygen-enriched air by means of a physical reaction as defined in the independent claims.

The object with regard to the device is also solved by the invention with an emergency oxygen supply arrangement. The object of the invention thus also leads to an emergency oxygen supply arrangement comprising said emergency oxygen supply mask. The invention recognizes that the emergency oxygen supply mask can be presented to the passenger in a variety of suitable ways. One possibility of presenting an emergency oxygen supply mask is dropping the mask from a passenger service unit wherein the emergency oxygen supply mask is connected to or not connected to an oxygen supply conduct to a common oxygen source. Another possibility is providing an oxygen supply mask in reach of a passenger such that the passenger will be able to grasp the mask in an emergency situation; e.g. a mask can be stored in or before a passenger's seat such that a passenger is readily able to grip one of the masks when necessary.

The object of the invention with regard to the method is achieved by the invention with a method as claimed in instant claim 15. The concept of the invention thus also leads to a method rescuing a passenger of an aircraft in emergency situation wherein an oxygen mask having a mask body is presented to the passenger wherein said oxygen mask drops out of a passenger service unit, and exhaled air out of said mask body is directed to a physical reaction component at least. Supply air is processed from the exhaled air in form of oxygen-enriched air or carbon dioxide depleted air out of said physical reaction component to the mask body and the physical reaction component is, in particular releasable, connected to a pressurized reservoir or manifold of air.

These and further developed configurations of the invention are further outlined in the dependent claims. Thereby, the mentioned advantages of the proposed concept are even more improved. For each feature of the dependent claims it is claimed independent protection independent from all other features of this disclosure.

In a particular preferred development the physical reaction component at least is an integral part of said oxygen mask and/or is adapted to self-sustained providing of breathable supply air to the first opening of the mask body. In a particular advantageous way thereby the passenger in an emergency situation can move away from his seat still being prevented to pass out from consciousness due to lack of oxygen; self-sustaining oxygen flow is still available even in situations where fire, dust or smoke is depleting ambient oxygen. In essence a passenger is able to move in hazardous situations over a comparably long distance and thus is able to reach an emergency exit in a more flexible and reliable way; in particular without being endangered to suffer from hypoxia.

Still also in a further preferred development, in particular for providing a start up oxygen supply, the mask body may provide a further opening releasable connectable to a common source of oxygen, in particular a flow conduct to a central common source of oxygen. In particular said second opening is further releasable connectable to a common source of oxygen. Thus, whereas a passenger is provided with high grade oxygen supply from a central oxygen source still also, as described above, the emergency oxygen supply mask of the invention allows the passenger to move away from his seat and proceed to an emergency exit once connection to the common source of oxygen is released and the passenger still is able to be provided with the self-sustained flow of oxygen-enriched supply air.

Preferably the supply mask comprises a physical reaction component with a number of flow beds enclosing said physical reaction material to receive a flow of exhaled air and provide a flow of oxygen-enriched air when receiving the exhaled air. Preferably a single, double or more than two flow beds are provided, in particular the physical reaction component comprises a number of more than two flow beds, in particular at least one nano-filter-bed and at least one sieve-bed. On the one hand due to the number of flow beds the development allows an improved adaptation of processing of the exhaled air to provide supply air and on the other hand still also keeps adapting improved supply air synchronized with the breathing rhythm of the passenger. Irregularities and fluctuations in oxygen flow are avoided and are averaged out with increasing number of flow beds in the physical reaction component.

Still also a single or double of two flow beds in the physical reaction component is affordable accompanied with a functionality, in particular a valve means, adapted to charge the single or the two flow beds with gas flow adapted to the breathing cycle of a passenger. In particular a functionality of the flow bed itself and/or a valve means is adapted to observe a phase shift between inhaling and exhaling when using the emergency oxygen supply mask.

In a particular preferred first variant of development a flow bed is a sieve-bed having an inlet first side and an outlet second side for exhaling, i.e. for passing through exhaled air, thus with regard to a direction of an exhaled air flow. The sieve-bed in a particular also has an inlet second side and an outlet first side for inhaling, i.e. for passing through inhaled air, thus with regard to a direction of an inhaled air flow. In other words the inlet first side and the outlet first side may be an identical side of construction of a single flow bed of the physical reaction component; respectively the outlet second side for exhaling and the inlet second side for inhaling may be an identical side of a single flow bed of the physical reaction component.

In particular the physical reaction component comprises a first sieve-bed and a second sieve-bed wherein in a first breathing cycle for exhaling the first sieve-bed is functioning as an adsorption bed, i.e. adapted to work by means of adsorption of $O_2$-gas, and for inhaling the second sieve-bed is functioning as a desorption bed, i.e. adapted to work by means of desorption of $O_2$-gas. Additionally or alternatively in a second breathing cycle for exhaling the second sieve-bed is functioning as an adsorption bed and for inhaling the first sieve-bed is functioning as a desorption bed. Thereby by adsorption and desorption in alternation the sieve-beds are fully or at least partly recovered by using a pressure alternation amplitude during phase shift between inhaling and exhaling of a passenger.

In a particularly preferred second variant of development the supply mask has a flow bed in form of a nano-filter-bed having a first, in particular raised, pressure first side for guiding a flow of exhaled air along the first side and a second, in particular lowered, pressure second side for conveying the oxygen-enriched air.

Whereas a sieve-bed is preferably build with a physical reaction material in form of a zeolite-based material it turns out that the filter-bed is preferably build with a physical reaction material in form of a nano-filter based material to form a filter tube bed, in particular a nano-tube bed. A zeolite-based material has been shown to be particular preferred for the sieve-bed adapted to work by means of adsorption and desorption of an $O_2$-gas fraction. The nano-filter based material has turned out to be particular preferred material in a filter tube bed adapted to work by means of molecular filtering of $O_2$ molecules from $N_2$ molecules.

Both variants are preferably adapted to provide an oxygen-enriched product gas stream for providing a supply air to the first opening of the mask body. In particular in the above-mentioned first variant of development it has been shown that a first and a second flow bed of at least two flow beds are preferably provided; in particular a double flow bed of nano-filter based material. Additionally or alternatively, in particular in the second variant of development, a first and a second side of at least two sides of a single flow bed are provided; in particular a single flow bed of zeolite-based material.

To provide a particular improved recovering of the physical reaction component a first flow bed and a second flow bed of at least two flow beds are provided and/or a first and a second side of at least two sides of a single flow bed are provided. In particular a flow path from at least two flow paths to the flow beds or sides is provided. Further additionally or alternatively an actuable switching valve means is adapted to charge said flow path selected from the at least two flow paths with a exhaled air in one breathing cycle and to charge another flow path selected from the at least two flow paths with inhaled air in another breathing cycle.

A sensor can be provided to actuate the actuable switching valve and/or the actuable switching valve is a self-actuating check valve. E.g. the sensor and/or the valve can be provided for detecting exhaled air by means of at least one of the parameters selected from the group consisting of: pressure, temperature, gas fraction content or the like parameters being significant for a flow of gas fraction.

In a particular preferred development the alternating pressure amplitude in a phase shift between exhaling and inhaling of a passenger can be used to be sensed by a pneumatic signalling sensor. Thus the sensor is particular preferred provided for detecting exhaled air by means of a pressure parameter and/or advantageously is formed as a pneumatically signalling sensor. Preferably the switching valve means is a pneumatical valve switching the flow of air from a first flow part to a second flow part and thus switching direction of air in a first and a second flow bed; in particular an alternating check valve or a back-pressure check valve can be provided.

Further also the sensor can be adapted to provide other signalling than pneumatical signalling, like for instance a electrical signalling and/or a optoelectronic signalling and/or a electro-mechanical signalling sensor can be used (e.g. a MEMS device or the kind) for providing a pressure sensor.

A further development provides for a particular equalized flow in the production gas stream either with a single flow bed or two flow beds or with a number of more than two flow beds. Whereas with increasing number of flow beds the flow of product stream is preferably equalized as compared to a lower number of flow beds still also the weight of an emergency oxygen supply mask is preferably kept as low as possible for convenience and handling purposes during a hazardous or emergency situation. A preferred light weight improvement is to provide an emergency oxygen supply mask by further comprising a flexible buffer, in particular an air bag, connected to said mask body.

Preferably said flexible buffer is connected to said mask body via said physical reaction component. By means of the air bag or the like flexible buffer a flow of product gas stream is equalized and fluctuations are diminished although still the number of flow beds can be kept as low as possible, in particular can be a single nano-filter filter tube bed or a zeolite sieve-bed.

Preferably the oxygen mask further comprises a chemical reaction component connected to the mask body for receiving exhaled air out of said mask body, converting said exhaled air into supply air by a chemical reaction between said exhaled air and a chemical reaction material comprised in said chemical reaction component to produce oxygen-enriched air and for supplying said oxygen-enriched air as the supply air to the first opening of the mask body.

Preferably the emergency oxygen supply mask is adapted for rescuing a passenger of an aircraft in an emergency situation, wherein:
- an exhaling valve is interconnected between the physical and/or a chemical reaction component and the flexible buffer,
- an inhaling valve is interconnected between the mask body and the flexible buffer,
- wherein said exhaling valve is adapted to open if a pressure in the physical and/or a chemical reaction component is higher than in the flexible buffer and to close if a pressure in the flexible buffer is higher than in the oxygen mask and
- wherein said inhaling valve is adapted to open if a pressure in the flexible buffer is higher than in the oxygen mask and to close if a pressure in the physical and/or chemical reaction component is higher than in the flexible buffer.

A particular preferred embodiment of the development provides for an emergency oxygen supply mask as claimed in claim 1 wherein the physical reaction component comprises a single bed of nano-filter based material as the physical reaction material or a first and a second flow bed of zeolite based sieve material as the physical reaction material. In particular in the former case the flow of gas is controlled by an back-pressure or other kind of check valve. In particular in the latter case the flow of gas is controlled by an alternating check valve or the like flip-flop or two way valve or other kind of check valve.

Still also notwithstanding the above-mentioned concept of the invention the physical reaction component can be combined with the chemical reaction component adapted to enrich an $O_2$ gas fraction to the exhaled air for converting said exhaled air into supply air. In particular the chemical reaction material is $KO_2$ in an exothermic reaction as follows:

$$4KO_2 + 2CO_2 = 2K_2CO_3 + 3O_2.$$

Thus, current dioxide contained in the exhaled air is chemically bound in the chemical reaction component and oxygen is produced therein. In the chemical reaction material in the chemical reaction component carbon dioxide is bound out of the exhaled air and oxygen is produced out of the exhaled air at the same time.

For a more complete understanding of the invention, the invention will now be described in detail with reference to the accompanying drawing. The detailed description will illustrate and describe what is considered as a preferred embodiment of the invention. It should of course be understood that various modifications and changes in form or detail could readily be made without departing from the spirit of the invention. It is therefore intended that the invention may not be limited to the exact form and detail shown and described herein, nor to anything less than the whole of the invention disclosed herein and as claimed hereinafter. Further the features described in the description, the drawing and the claims disclosing the invention may be essential for the invention considered alone or in combination. In particular, any reference signs in the claims shall not be construed as limiting the scope of the invention. The wording "comprising" does not exclude other elements or steps. The wording "a" or "an" does not exclude a plurality. The wording, "a number of" items, comprises also the number one, i.e. a single item, and further numbers like two, three, four and so forth.

BRIEF DESCRIPTION OF THE DRAWINGS

The drawing shows in.

DETAILED DESCRIPTION OF THE DRAWINGS

For identical or equivalent items or items of identical or equivalent function in the following the same reference marks are used. For corresponding features thus it is referred to the above description. In the following, in particular the differences between the embodiments of different Fig.'s are described.

Figure 1:
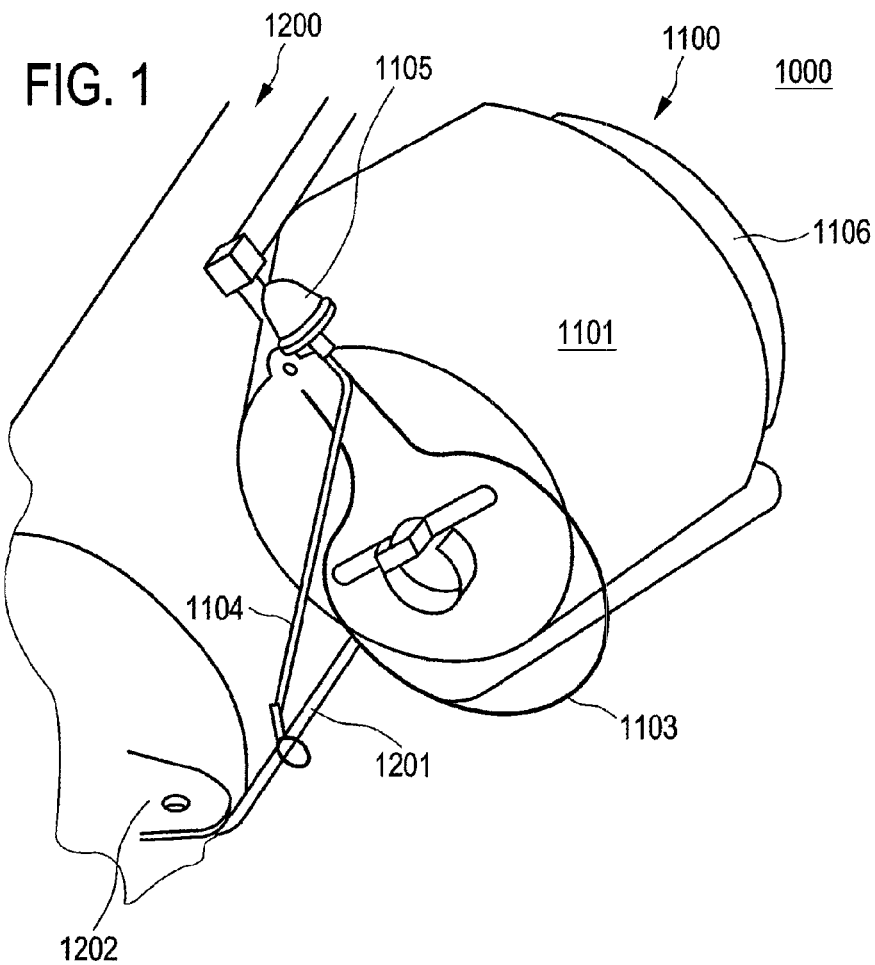
FIG. 1: a scheme of a comparative embodiment of an emergency oxygen supply mask.

FIG. 1 shows schematically a comparative emergency oxygen supply system with an emergency oxygen supply mask 1100 and an emergency oxygen source 1200 assigned to at least the emergency oxygen supply mask 1100 shown with a mask body 1101 and an oxygen bag 1106 stuffed into the inner side of the mask body 1101 in FIG. 1, wherein the oxygen source is formed as a chemical oxygen generator (COG). The oxygen source 1200 usually is accommodated with a number of further emergency oxygen supply masks 1100 in an oxygen supply container of a passenger service unit 1000 which is not shown in detail. Once the emergency oxygen supply mask 1100 drops with its mask body 1101 and the oxygen bag 1106 connected to the front outer side of the mask body 1101 from the passenger service unit's 1000 container the oxygen mask body 1101 is still connected via a first lanyard 1103 and a second lanyard 1104 to an activation line 1201 of the oxygen source 1200, namely for actuating an activation assembly 1202 for starting a short exothermic reaction which is sufficient to initiate the chemical reaction inside the oxygen generator 1200 to produce oxygen.

Whereas the first lanyard 1103 determines the level to which the oxygen mask body 1101 falls out of the casing in case of an emergency situation the second lanyard 1104 connects a fixation plug 1105 to the activation line 1201 to actuate the actuation mechanism 1202 for starting the oxygen generating reaction. Oxygen is then provided via a hose and oxygen gas fraction interfaces (not shown) first to the oxygen bag 1106 assigned to the mask body 1101 when being unfolded from the inner side of mask to the front outer side of the mask body 1101 upon drop out of the mask. Thus direct oxygen flow from the chemical oxygen generator of the oxygen source 1200 is provided via the oxygen bag 1106 on a front outer side of the mask body 1101 to a first large opening of the mask body 1101 for covering mouth and/or nose of the passenger to supply the passenger with high grade oxygen during a hazardous or emergency situation.

Figure 2:
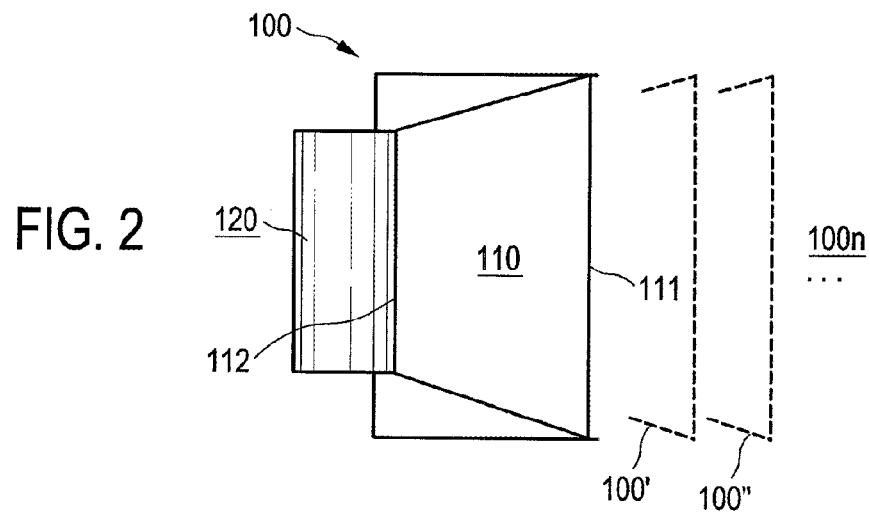
FIG. 2: a general embodiment of an emergency oxygen supply mask in a principle view graph.

FIG. 2 shows schematically an embodiment of an emergency oxygen supply mask 100 with a mask body 110 and a physical reaction component 120 being an integral part of said oxygen mask 100 and wherein the mask 100 is adapted to self-sustained providing of breathable supply air to the first opening 111 of the mask body 110 via a second opening 112 connecting to said first opening 111 for providing breathable supply air. Optionally, in general, any of this kind of this mask 100 also can be supplemented with a breather bag, which is not shown in FIG. 2. The emergency oxygen supply mask 100, with or without breather bag, can be accommodated in an oxygen system container of the passenger service unit 100n; in that the mask 100 is one part of an emergency oxygen supply arrangement with a further number of emergency oxygen supply masks 100', 100" . . . 100$^{(n)}$ which are shown in dashed line schematically also in FIG. 2.

Figure 3:
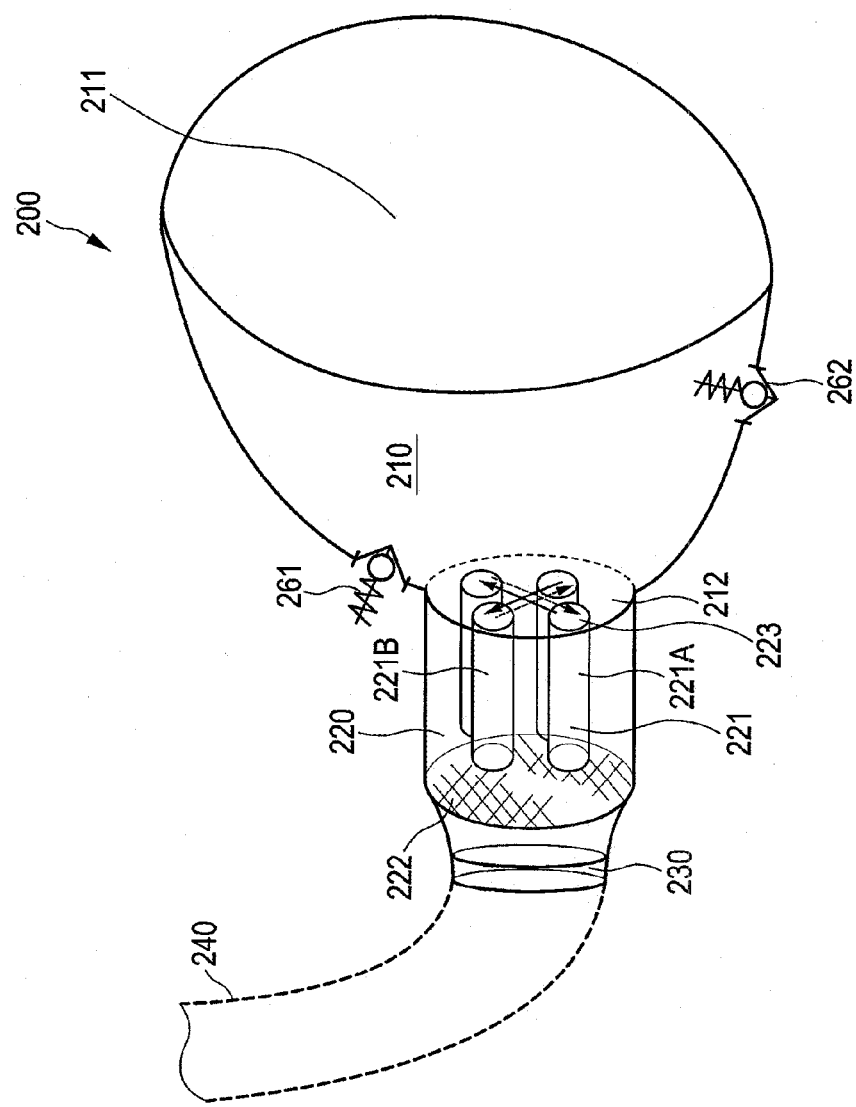
FIG. 3: a first embodiment of an emergency oxygen supply mask according to a first variant of a development of the invention in a schematic view.

FIG. 3 shows a first preferred embodiment according to a first developed variant wherein an emergency oxygen supply mask 200 is provided with a mask body 210 with a first opening 211 for covering mouth and/or nose of the passenger and with a second opening 212 connecting said first opening 211 for providing breathable supply air. The oxygen mask 200 comprises a physical reaction component 220 connected to the mask body 210 for receiving exhaled air out of said mask body 210 converting said exhaled air into supply air by a physical reaction between said exhaled air and a physical reaction material 221 in said physical reaction component 220 to produce oxygen-enriched air and for supplying said oxygen-enriched air as the supply air to the first opening 211 of the mask body 210. In this embodiment the physical reaction component is further supplemented with a filter cup 222 adapted to remove particles, e.g. dust particles or fume particles or the like, from ambient air when ambient air is sucked into the physical reaction component 220. Also, optionally, in addition or in exchange, e.g. connectable to, the filter cup 222 is a reservoir or manifold of pressurized air, which can be used to further provide breathable air to the passenger; e.g. bleed air of the aircraft.

Further the physical reaction component 220 is accompanied with a further opening 230 on the mask body 210 adapted to be releasable connectable to a common source of pressurized air like for instance via a flow connection line 240. Also, in alternative, further opening 230 can be releasable connected to receive fresh oxygen from an oxygen generator like a chemical oxygen generator or the like in a passenger service unit. Also the further opening 230 and/or the flow connection line 240 can be connected to an oxygen bag like the one shown in FIG. 1, which is not shown in detail here.

The functioning of the movable and self-sustained emergency oxygen supply mask 200 is as follows. Usually passengers, while the masks are being used, shall not leave their seat for any reasons until it is save to breath without emergency oxygen. If there is a fire on board of the aircraft, masks are not deployed as the production of oxygen may further fuel the fire. However still, nevertheless in a hazardous emergency situation passengers have to leave the airplane or at least approach an emergency exit safely without being affected by the danger of hypoxia. Thus the emergency oxygen supply mask 200 shown in FIG. 2 is provided with a releasable connection interface from the common source of pressurized air to the opening 230. Also the passenger, after disconnecting the flow connection line 240 from the releasable connection interface 230, can take the emergency oxygen supply mask 200 with him, while keeping covered mouth and/or nose with the mask first opening 211 when moving to the emergency exit e.g. or some other place in the air craft cabin.

Still nevertheless a passenger will be able to receive filtered air at least from ambient air as drawn through the filter cup 222 and thus free from any dust or fume particles. As can be seen from the full line arrows, firstly—during an inhaling breathing cycle—ambient air is drawn through a first zeolite sieve-bed 221A and by desorption oxygen stored in the zeolite sieve-bed 221A is enriched with oxygen and/or filtered to the inhaled air and thus can be breathed by the passenger from the first opening 211. As can be seen along the second full line arrows, secondly—during an exhaling breathing cycle—the passenger may press exhalation air into the second zeolite sieve-bed 221B, wherein remaining oxygen content thereof can be absorbed into the second zeolite sieve-bed 221B thereby.

During a breathing pause, e.g. actuated with rising slope of an inhalation process a check valve 223 is switched to a position such that an air flow through the first and second sieve-bed 221A, 221B along the dashed arrows is possible. Namely when inhaling now oxygen can be drawn from ambient air through the filter cup 222 and thus, free of fume or other dust particles, is drawn through the second sieve-bed 221B. Thereby ambient air is enriched with oxygen and/or filtered from the second sieve-bed 221B by desorption. Thus a passenger will be able to breath the oxygen-enriched air arriving into the first opening 211 of the oxygen mask 200. In the exhaling cycle now the exhaled air is pushed along the second dashed arrow into the first sieve-bed 221A thereby absorbing oxygen into the first sieve-bed 221A and then excess air is moved out of the physical reaction component through the filter cup 222.

Thereafter, again, during a breathing pause with rising slope of an inhale breathing the check valve 223 again is switched to allow air flow directly in as indicated with the full line arrows according to the description outlined hereinbefore. Also a first outlet back-pressure check valve 261 is provided to the mask body 210 in order to let exhaled air escape from the first opening 211 of the oxygen mask 200 mask body 210 in a situation where the flow through physical reaction component 220 may be insufficient, in particular in a non-stationary use of the oxygen mask 200. Also a second inlet back-pressure check valve 262 is provided in order to let air to inhale into the first opening 211 of the oxygen mask 200 mask body 210 in a situation where the flow through physical reaction component 220 may be insufficient, in particular in a non-stationary use of the oxygen mask 200.

Consequently, starting from a rest oxygen flow available from the connecting line 240 to a connection interface of further opening 230 a passenger is able to extract sufficient oxygen from ambient atmosphere by means of the concentrator function of the physical reaction component 220. As will be seen from FIG. 4 as described hereinbelow further a re-breather functionality can be provided by means of a buffer to the physical reaction component 220. The above measures at least are sufficient to allow the passenger to approach an emergency exit and thus escaping an airplane in a hazardous situation and avoiding the danger of hypoxia. Further the oxygen mask 200 is providing oxygen to a passenger's nose or mouth free of particles arising from a dusty and fume ambient atmosphere.

Figure 4:
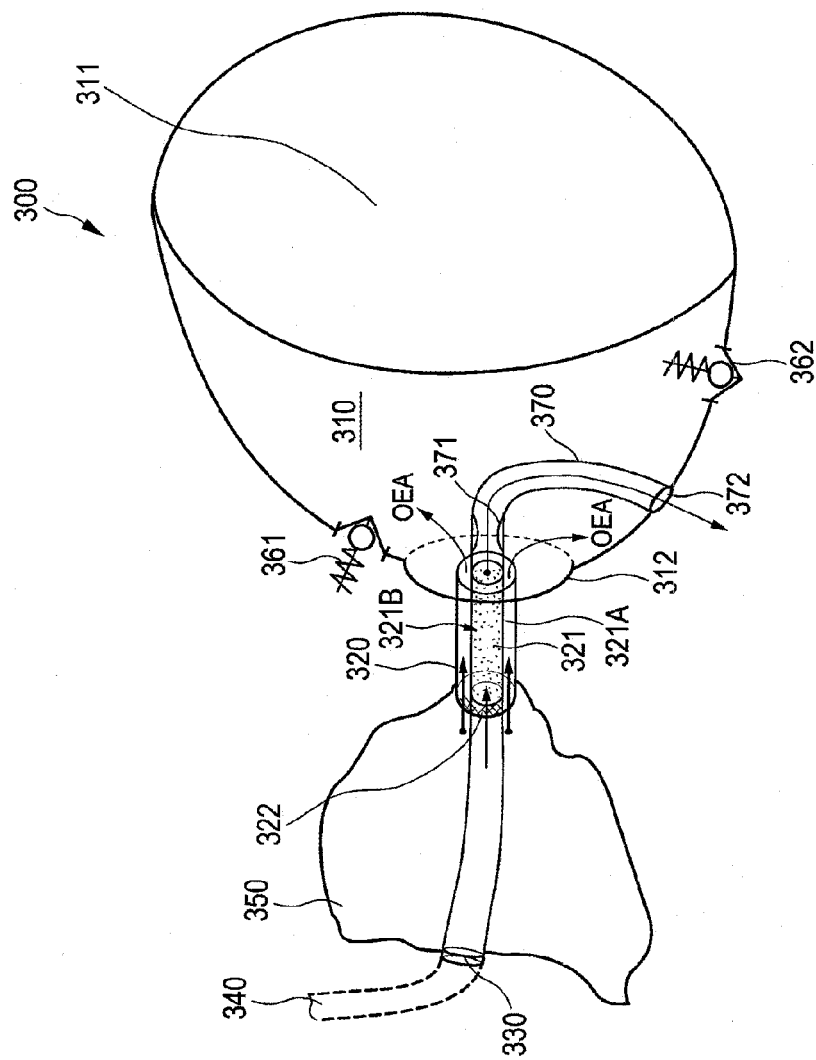
FIG. 4: a second embodiment of an emergency oxygen supply mask according to a second variant of a development of the invention in a schematic view.

FIG. 4 shows a second embodiment of an emergency oxygen supply mask according to a second variant of a development wherein the emergency oxygen supply mask 300 again has a mask body 310 with a first opening 311 for covering mouth and/or nose of the passenger and with a second opening 312 connecting said first opening 311 for providing breathable supply air. The oxygen mask 300 further comprises a physical reaction component 320 connected to the mask body 310 for receiving exhaled air out of said mask body 310 converting said exhaled air into supply air by a physical reaction between said exhaled air and the physical reaction material comprised in said physical reaction component 320 upon receipt of pressurized air. Thereby oxygen-enriched air is produced for supplying said oxygen-enriched air as the supply air to the first opening 311 of the mask body. In the second embodiment the physical reaction material is formed by a single flow bed of nano-filter based material—here a nano-tube material—adapted to work by means of molecular filtering of $O_2$ molecules from $N_2$ molecules.

Further the physical reaction component 320 provides a filter cup 322, for instance comprising activated charcoal, for purging ambient air and filtering fume, dust and other particles from ambient air, in the case ambient air is drawn through the filter cup 322 from outside. Also the filter cup 322 may serve as an antisuffication vent in addition or in alternative to the antisuffication vent on the mask body 310, namely in form of the back-pressure check valve 262. Connected to the physical reaction component 320 via the filter cup 322 is a re-breather bag or any other kind of flexible buffer 350 adapted to receive and supply for a rebreathing of formerly exhaled air, in particular in the case the mask 300 is in a non-stationary use. Also, optionally, in addition or in exchange, e.g. connectable to, the filter cup 322 is a reservoir of pressurized air, which can be used to further provide breathable air to the passenger for instance via a flow connection line 340 releasable connected via the further opening 330.

The functioning of the second embodiment of an emergency oxygen supply mask 300 is as follows: In a non-stationary use, once being disconnected from an air flow connection line 340 the further opening 330—wherein also the further opening 330 and/or the flow connection line 340 can be connected to an oxygen bag like the one shown in FIG. 1, which is not shown in detail here—may be closed by a back-pressure check valve. Then the passenger is able to use the physical reaction component 320 for rebreathing and oxygen concentration or at least as a filter to provide supply air to the first opening 311 of the emergency oxygen supply mask body 310 in basically the similar manner as described with FIG. 3.

In case of a stationary use when exhaling exhaled air can be pressed through first outlet back-pressure check valve 361. An inner cylinder 321B of the physical reaction component 320 receives pressurized air from connection line 340 thereby filling the buffer 350 due to—effected by the nano-filter based material—molecular filtering of $O_2$ molecules from $N_2$ molecules and consequently providing enriched oxygen atmosphere in the outer ring space 321A of the physical reaction component 320. Oxygen-depleted air is guided through line 370 via a throttle 371 to outlet 372 from the inner cylinder 321B without being mixed with enriched supply air in the first opening 311. Oxygen enriched supply air (OEA) in the first opening 311 is supplied via the outer ring space 321A from the physical reaction component 320 as shown by the solid arrows. Thereafter exhaled air can be pressed through first outlet back-pressure check valve 361 again. Also a second inlet back-pressure check valve 362 is provided in order to let air to inhale into the first opening 311 of the oxygen mask 300 mask body 310 in a situation where the flow through physical reaction component 320 may be insufficient, in particular in a non-stationary use of the oxygen mask 300.

Even when disconnected from pressurized air during pause of an inhalation half cycle an alternating check valve can be switched such that a passenger can inhale air from the re-breather bag in form of the buffer 350 through the outer ring space 321A of the physical reaction component 320 being enriched with oxygen as described hereinbefore with the first exhaling breathing half cycle.

Thereafter again—preferably after having switched the alternating check valve—during a breathing pause to the next exhaling breathing cycle the passenger again will be able to exhale air through the first outlet back-pressure check valve 361.

Thus,—even in a non-stationary use at least partly—after a single or two full breathing cycles of inhaling and exhaling the re-breather bag in form of the buffer 350 will be able to buffer practically full oxygen content breathing air to supply oxygen-enriched supply air to the first opening 311 of the breathing emergency oxygen supply mask 310.

Also, as indicated before, the buffer 350 is connected to the physical reaction component 320 by means of the filter ring 322. Thus also ambient air can be sucked through the filter ring 322 directly to the outer ring space 321A of the physical reaction material 321. Thus even though the ambient air might not provide sufficient oxygen, nevertheless—accompanied with the enriched oxygen from the buffer—still the passenger will be able to use the oxygen mask when moving from his place in the airplane to an emergency exit in a hazardous situation and thus the passenger moves without danger of hypoxia as it would have been the case without oxygen mask.

Of course also, acknowledging that usually an aircraft in a controlled emergency descend to a lower altitude will afford breathing without emergency oxygen the processes described above with the oxygen masks shown in FIG. 3 and FIG. 4 can be used to provide passengers with sufficient oxygen supply air without endangering a hypoxia in the case a central oxygen supply may fail or fail to last for a sufficient time period of controlled descend.

It is to be understood that the aforementioned embodiments can be supplemented by means of a chemical reaction component adapted to enrich an $O_2$-gas fraction to the exhaled air for converting said exhaled air into supply air, in particular in that the chemical reaction material is $KO_2$. The oxygen mask further can comprise a chemical reaction component in addition to the physical reaction component 220, 320 connected to the mask body for receiving exhaled air out of said mask body, converting said exhaled air into supply air by a chemical reaction between said exhaled air and a chemical reaction material comprised in said chemical reaction component to produce oxygen-enriched air and for supplying said oxygen-enriched air as the supply air to the first opening of the mask body.

In summary the masks 100, 200, 300 shown in FIG. 2 to FIG. 4 of the drawing allow more flexibility and mobility of a passenger without endangering a hypoxia in an emergency situation like in particular a long term controlled descend or a hazardous situation for leaving an airplane and still provide safe supply of oxygen-enriched air in a stationary use at least as long as necessary.

The invention claimed is:

1. Emergency oxygen supply mask adapted for rescuing a passenger of an aircraft in an emergency situation, comprising:
    an oxygen mask having a mask body with a first opening for covering at least one of a mouth and a nose of the passenger and with a second opening connecting to said first opening for providing a breathable supply air,
    a physical reaction component connected to the mask body for receiving air, said air comprising exhaled air out of said mask body, adapted for converting said air into the breathable supply air by a physical reaction between said air and a physical reaction material in said physical reaction component to produce oxygen-enriched air and for supplying said oxygen-enriched air as the supply air to the first opening of the mask body, wherein:
    the physical reaction component comprises a number of flow beds enclosing said physical reaction material to receive the air and provide the oxygen-enriched air when receiving the air and wherein each of the number of flow beds is a sieve-bed having an inlet first side and an outlet second side for passing through the air and an outlet first side and an inlet second side for passing through the breathable supply air;
    the physical reaction component is releasably connected to a pressurized reservoir or manifold of air;
    the physical reaction component provides a flow path from at least a first flow path and a second flow path to the number of flow beds;
    an actuable switching valve integral to the mask body is adapted to change said flow path between the first flow path and the second flow path; and
    each of the number of flow beds comprises a first sieve-bed and a second sieve-bed, and:
    in a first breathing cycle, the actuable switching valve provides the first flow path in which the first sieve-bed functions as an adsorption bed for exhaled air and the second sieve-bed functions as a desorption bed for inhaled air, and
    in a second breathing cycle, the actuable switching valve provides the second flow path in which the second sieve-bed functions as an adsorption bed for exhaled air and the first sieve-bed functions as a desorption bed for inhaled air.

2. Supply mask according to claim 1, wherein the actuable switching valve is a self-actuating check valve.

3. Supply mask according to claim 1, wherein said oxygen mask further comprises at least one of a flexible buffer and a bag, wherein the at least one of a flexible buffer and a bag is connected to said mask body via said physical reaction component.

4. Supply mask according to claim 1, wherein at least one of a filter and the number of flow beds is adapted to deplete a $CO_2$-gas fraction from the air to provide the oxygen-enriched air for converting said air into the breathable supply air, wherein the at least one of the filter and the number of flow beds comprises activated charcoal.

5. Supply mask according to claim 1, wherein the physical reaction component is adapted to work by means of adsorption and desorption of an $O_2$-gas fraction and comprises the physical reaction material in form of a zeolite-based material.

6. Supply mask according to claim 1, wherein at least one of the physical reaction component and a chemical reaction component is an integral part of said oxygen mask and is an integral part of the mask body and/or is adapted for self-sustained providing of the breathable supply air to the first opening of the mask body.

7. Supply mask according to claim 1, wherein a further opening of the mask body is releasably connectable to at least one of a common source of oxygen and pressurized air, wherein said second opening is further releasably connectable to at least one of the common source of oxygen and the pressurized air.

8. The supply mask according to claim 2, wherein the actuable switching valve is provided for detecting the exhaled air by at least one parameter selected from the group consisting of: pressure, temperature, and gas fraction content.

9. The supply mask according to claim 1, further comprising a chemical reaction component configured to convert exhaled air into the breathable supply air by a chemical reaction between said air and a chemical reaction material in the chemical reaction component to produce oxygen-enriched air and for supplying said oxygen-enriched air as the supply air to the first opening of the mask body, and wherein the chemical reaction component is an integral part of the mask body.

* * * * *